US00PP11571P

United States Patent [19]

Laver

[11] Patent Number: Plant 11,571

[45] Date of Patent: Oct. 17, 2000

[54] MINIATURE ROSE PLANT NAMED 'FALL FESTIVAL'

[75] Inventor: Keith Laver, Caledon East, Canada

[73] Assignee: CP (Delaware), Inc., Wilmington, Del.

[21] Appl. No.: 09/231,090

[22] Filed: Jan. 14, 1999

[51] Int. Cl.[7] ..... A01H 5/00

[52] U.S. Cl. ..... Plt./116; Plt./123

[58] Field of Search ..... Plt./116, 123, 141, Plt./143

*Primary Examiner*—Howard J. Locker

*Attorney, Agent, or Firm*—Burns, Doane, Swecker & Mathis, L.L.P.

[57] ABSTRACT

A new and distinct variety of rose plant of the Miniature Class is provided which abundantly forms attractive striped red and yellow-orange blossoms on a substantially continuous basis. A very dense, upright and bushy growth habit is exhibited that renders the plant particularly well suited for growing as a potted plant in the greenhouse. The bicolored buds are pointed. The variety is particularly well suited for growing as distinctive striped bicolored potted rose plant in view of its good blooming qualities.

1 Drawing Sheet

SUMMARY OF THE INVENTION

The new variety of *Rosa hybrida* Miniature rose plant was created by artificial pollination wherein two parents were crossed which previously had been studied in the hope that they would contribute the desired characteristics. The female parent (i.e., the seed parent) of the new variety was an unnamed striped seedling from Springwood Miniature Roses (non-patented in the United States). The male parent (i.e., the pollen parent) of the new variety was the 'Springwood Red Victor' variety (non-patented in the United States). The parentage of the new variety can be summarized as follows:

Unnamed Striped Seedling×'Springwood Red Victor'.

The seeds resulting from the above pollination were sown and small plants were obtained which were physically and biologically different from each other. Selective study resulted in the identification of a single plant of the new variety.

It was found that the new variety of Miniature rose plant of the present invention possesses the following combination of characteristics:

(a) forms pointed bicolored buds,
(b) forms in abundance attractive striped red and yellow-orange blossoms,
(c) exhibits a very dense, upright and bushy growth habit, and
(d) forms attractive satiny foliage.

A distinctive striped rose plant is provided which is particularly suited for production by the pot plant industry in view of its good blooming qualities. The blossoming is consistent and reliable in nature.

The new variety well meets the needs of the horticultural industry. It also can be grown in the landscape provided it is sprayed to prevent Powdery Mildew.

The new variety has been found to undergo asexual propagation by a number of routes, including budding, grafting, and cuttage. Asexual propagation by the above-mentioned methods at Caledon East, Ontario, Canada and at West Grove, Pa., U.S.A., has shown that the characteristics of the new variety are strictly transmissible from one generation to another.

The New Variety has been named the 'Fall Festival' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during July while growing on their own roots indoors at West Grove, Pa. The weather had been unseasonably warm and very humid for the preceding five days. Under more typical growing conditions the bloom coloration would have commonly been even more vibrant.

FIG. 1 — illustrates a specimen of a young shoot;

FIG. 2 — illustrates a specimen of a floral bud with foliage before the opening of the sepals;

FIG. 3 — illustrates a specimen of a floral bud with foliage at the opening of the sepals;

FIG. 4 — illustrates a specimen of a floral bud with foliage at the opening of the petals;

FIG. 5 — illustrates a specimen of a flower with foliage during the initial course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates specimens of a main branch;

FIG. 14 — illustrates a specimen of a leaf with three leaflets — plan view — upper surface;

FIG. 15 — illustrates a specimen of a leaf with five leaflets — plan view — upper surface;

FIG. 16 — illustrates a specimen of a leaf with seven leaflets — plan view — under surface; and FIG. 17 — illustrates specimens of mature floral petals.

DETAILED DESCRIPTION

Figures 1, 2, 3, 4, 5, 6, 7, 8, 9, 10, 11, 12, 13, 14, 15, 16:
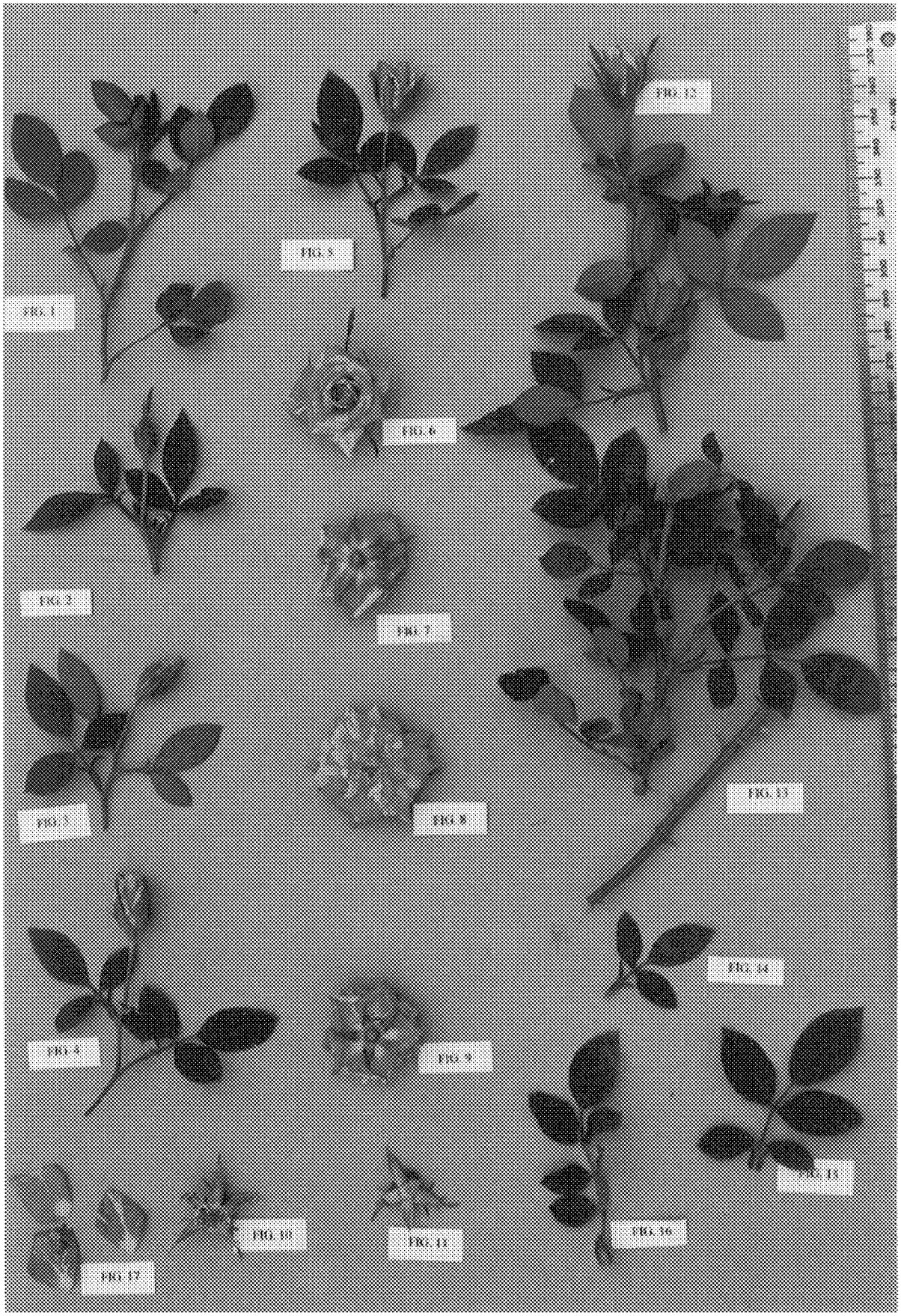

The chart used in the identification of the colors is that of The Royal Horticultural Society (R.H.S. Colour Chart). The description is based on two year-old specimens of the new variety which were observed during October while growing on their own roots outdoors at West Grove, Pa.

Class: Miniature adapted for pot forcing.

Plant:

*Height.*—Approximately 60 cm. on average at the end of the growing season.

*Width.*—Approximately 45 cm. on average at the end of the growing season.

*Habit.*—Upright and bushy.

Branches:

*Color.*—Young stems: near Yellow-Green Group 144A. Adult wood: Green Group 143A.

*Thorns.*—Size small. Quantity: medium as illustrated. Color: Greyed-Orange Group 177A.

Leaves:

*Petioles.*—Upper surface: Yellow-Green Group 144B. Under surface: Yellow-Green Group 144B, with stripes of Greyed-Red Group 178B.

*Stipules.*—Lower one-half is semi-circular, and narrows to the apex with auricle facing outward. The stipules tend to be wider and longer than those present on a typical Miniature rose plant.

*Leaflets.*—Number: 3 , 5, 7, and 9. Shape: Elliptical with a serrulate margin. Texture: Consistent. Serration: Regular (as illustrated). Size: Approximately 2.5 cm in length and approximately 1.5 cm in width. General appearance: Very dense, and grass green with a satiny finish. Color (young foliage): Upper surface: Between Green Group 137B and Green Group 137C. Under surface: Green Group 139D with veination of Green Group 138B. Color (adult foliage): Upper surface: Commonly between Green Group 135A and Green Group 137A. Under surface: Green Group 138A with veination of Green Group 138D.

Inflorescence:

*Number of flowers.*—Commonly approximately 3 to 5 per stem.

*Peduncle.*—Medium, Yellow-Green Group 144A in coloration, without prickles, and the length is approximately 3.5 cm. on average.

*Sepals.*—Upper surface: Yellow-Green Group 144B. The sepals commonly possess some short extensions (as illustrated). Under surface: commonly a blend of Green Group 138B and Yellow-Green Group 145A.

*Buds.*—Shape: Pointed. Length: Approximately 1.5 cm. on average. Size: small. Color upon opening: Upper surface: Red Group 42B striped with stripes of Yellow-Orange Group 23B. Under surface: Red Group 42A with highlights of Yellow Group 13B.

*Flower.*—Form: Double and imbricate. Diameter: Approximately 5 cm. on average. Color (when opening begins): Upper surface: Red Group 42B with stripes of Yellow-Orange Group 23B. Under surface: Red Group 42A with highlights of Yellow Group 13B. Color (when blooming): Upper surface: A blend of Red Group 42B and Yellow-Orange Group 23B. Under surface: A blend of Orange-Red Group 34A and Yellow-Orange Group 15C. Color (at end of opening): Upper surface: A blend of Red Group 43C, Red Group 47C, and Yellow-Orange Group 22C. Under surface: A blend of Yellow Group 12B and Red Group 47A. Petal shape: Elliptical. Fragrance: Light Tea Rose. Petal number: Approximately 26 on average. Anthers: Yellow-Orange Group 14B. Stamen number: Approximately 85 on average. Filaments: Yellow-Orange Group 16A. Pistil number: Approximately 30 on average. Stigmas: Yellow-Orange Group 14C. Styles: Red Group 40B. Receptacle: Yellow-Green Group 144B and in longitudinal section in the shape of a teardrop. Lasting quality: Long shelf life indoors. The blossoms commonly last approximately 5 days on the plant and approximately 5 days when cut and placed in a vase.

Development:

*Vegetation.*—Vigorous.

*Blooming.*—Abundant.

*Resistance to diseases.*—Good resistance to cylindrocladium and phytopthora root rot. When grown in the garden spraying for Powdery Mildew is recommended.

*Propensity to form hips/seed.*—None observed to date.

I claim:

1. A new and distinct variety of Miniature rose plant characterized by the following combination of characteristics:

(a) forms pointed bicolored buds,
(b) forms in abundance attractive striped red and yellow-orange blossoms,
(c) exhibits a very dense, upright and bushy growth habit, and
(d) forms attractive satiny foliage;

substantially as herein shown and described.

* * * * *